United States Patent [19]
Banas et al.

[11] Patent Number: 5,628,786
[45] Date of Patent: May 13, 1997

[54] RADIALLY EXPANDABLE VASCULAR GRAFT WITH RESISTANCE TO LONGITUDINAL COMPRESSION AND METHOD OF MAKING SAME

[75] Inventors: Christopher E. Banas; Scott Randall, both of Mesa; Tarun J. Edwin, Chandler; Fariba Hurry, Tempe, all of Ariz.

[73] Assignee: Impra, Inc., Tempe, Ariz.

[21] Appl. No.: 439,853

[22] Filed: May 12, 1995

[51] Int. Cl.$^6$ ............................................. A61F 2/06
[52] U.S. Cl. ............................ 623/1; 623/11; 623/12; 623/901; 428/422
[58] Field of Search .................... 428/422, 35.7; 623/1, 11, 12, 901

[56] References Cited

U.S. PATENT DOCUMENTS

| | | | |
|---|---|---|---|
| 3,400,719 | 9/1968 | Buddecke | 128/334 |
| 4,208,745 | 6/1980 | Okita | 3/1.4 |
| 4,229,838 | 10/1980 | Mano | 3/1.4 |
| 4,304,010 | 12/1981 | Mano | 3/1.4 |
| 4,306,318 | 12/1981 | Mano et al. | 3/1.4 |
| 4,447,570 | 5/1984 | Cook et al. | 524/127 |
| 4,550,447 | 11/1985 | Seiler, Jr. et al. | 623/1 |
| 4,647,416 | 3/1987 | Seiler, Jr. et al. | 264/118 |
| 4,728,328 | 3/1988 | Hughes et al. | 623/12 |
| 4,749,585 | 6/1988 | Greco et al. | 427/2 |
| 4,776,853 | 10/1988 | Klement et al. | 8/94.11 |
| 4,834,747 | 5/1989 | Gogolewski | 623/1 |
| 4,892,544 | 1/1990 | Frisch | 623/11 |
| 4,902,290 | 2/1990 | Fleckenstein | 623/1 |
| 5,061,276 | 10/1991 | Tu et al. | 623/1 |
| 5,094,806 | 3/1992 | Laughner | 264/523 |
| 5,118,524 | 6/1992 | Thompson et al. | 623/1 X |
| 5,282,847 | 2/1994 | Trescony et al. | 623/1 |
| 5,330,782 | 7/1994 | Kanazawa | 623/1 X |
| 5,383,927 | 1/1995 | De Goicoechea et al. | 623/1 |
| 5,413,598 | 5/1995 | Moreland | 623/1 |
| 5,476,506 | 12/1995 | Lunn | 623/1 |

*Primary Examiner*—Daniel Zirker
*Attorney, Agent, or Firm*—David G. Rosenbaum

[57] ABSTRACT

A microporous polytetrafluoroethylene ("PTFE") endovascular graft which has a reinforcing structure integrally bound to the graft which permits radial expansion of the graft and stabilizes the graft against longitudinal compression upon application of an axial force thereto and against axial foreshortening upon radial expansion of the graft. The graft is particularly useful as a covering for an endovascular stent.

19 Claims, 2 Drawing Sheets

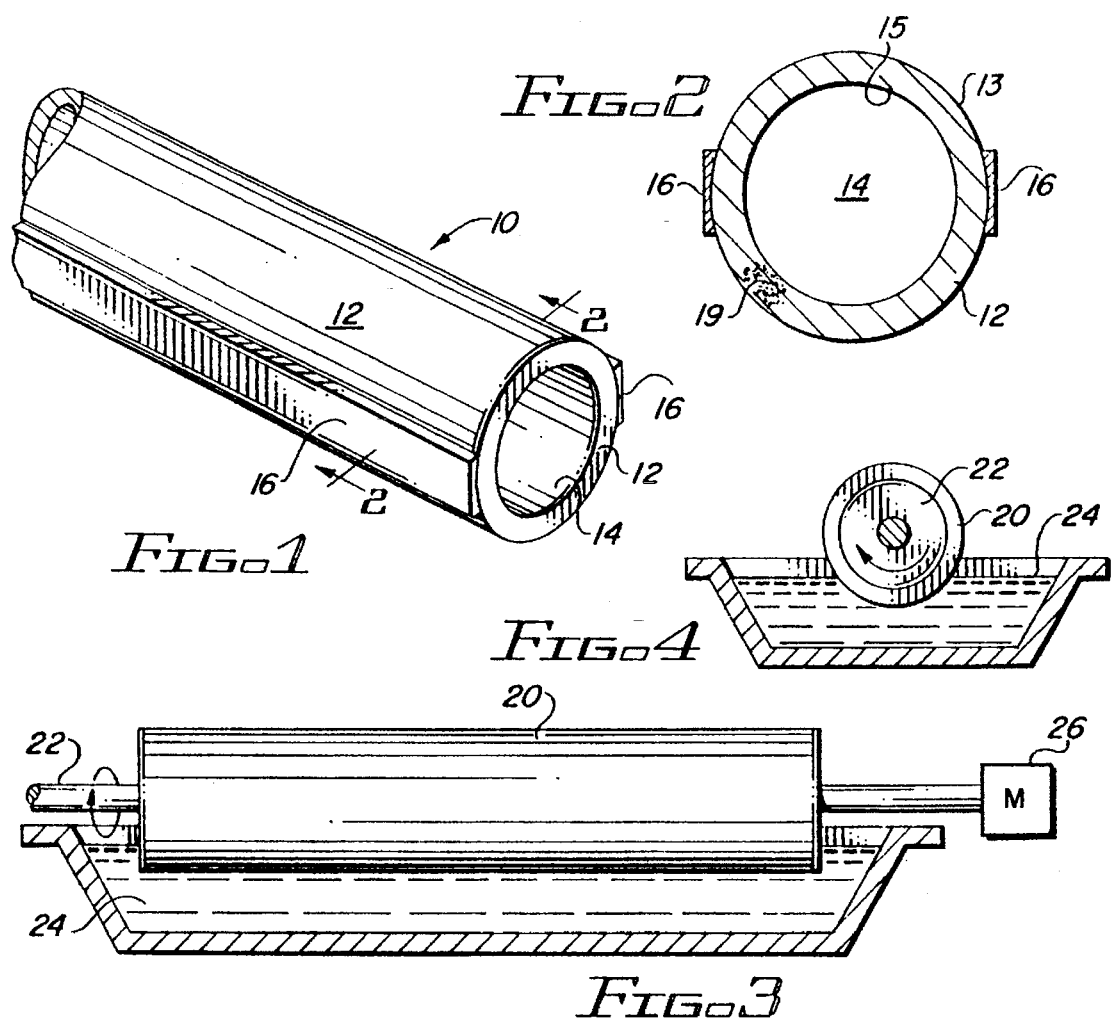
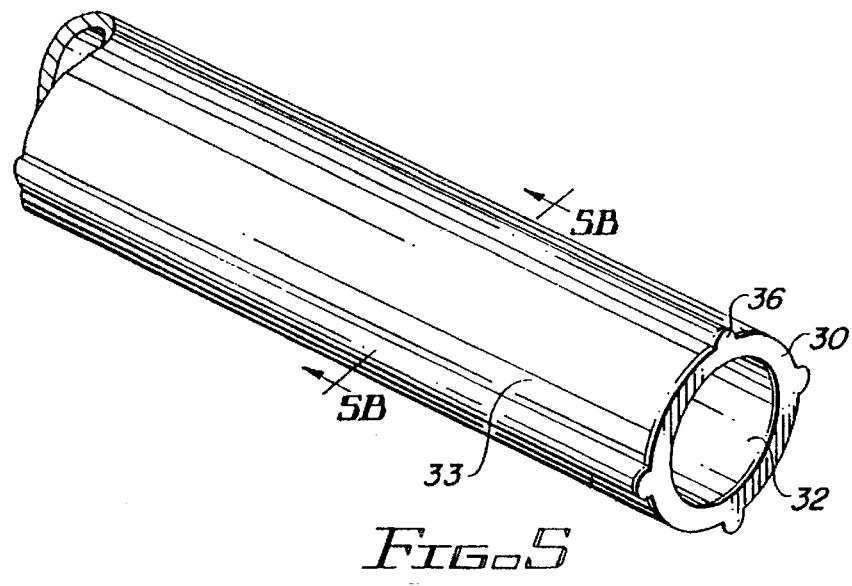

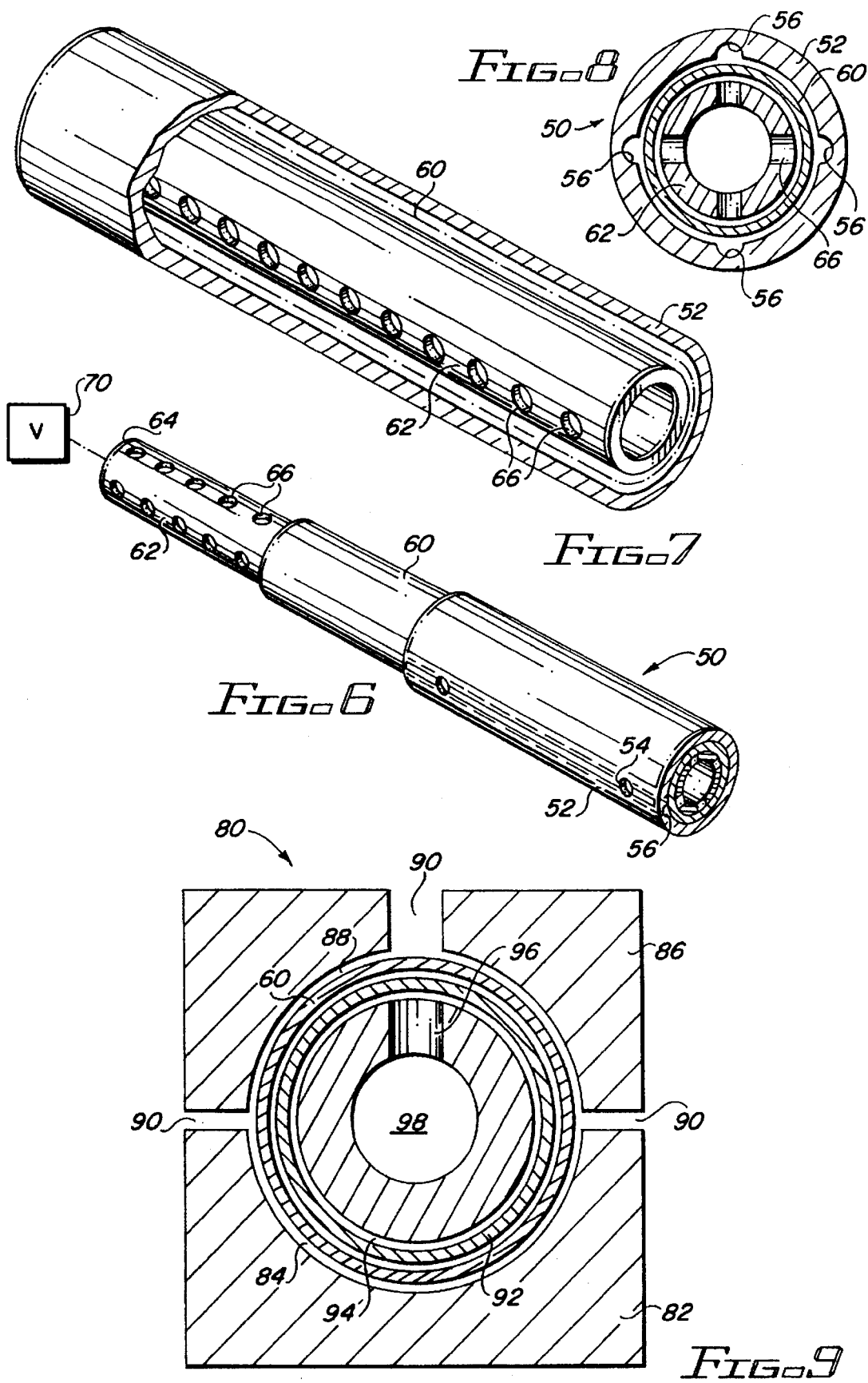

RADIALLY EXPANDABLE VASCULAR GRAFT WITH RESISTANCE TO LONGITUDINAL COMPRESSION AND METHOD OF MAKING SAME

BACKGROUND OF THE INVENTION

The present invention relates generally to radially expandable tubular grafts which are resistant to longitudinal compression resulting from an axially applied external force, and is resistant to axial shrinkage or axial foreshortening upon radial expansion. More particularly, the present invention relates to a microporous polytetrafluoroethylene ("PTFE") endovascular graft which has a reinforcing structure integral with or bound to the graft which permits radial expansion of the graft and stabilizes the graft against axial shrinkage upon radial expansion of the graft. Resistance to axial shrinkage is particularly desirable where a vascular graft is mounted onto a radially expandable endoluminal stent or alone onto an expansion balloon for intraluminal delivery and radial expansion.

The term "longitudinal compression" means a reduction in a longitudinal dimension resulting from an axially applied external force.

Radially expandable stents are used to maintain an occluded anatomical passageway in an unoccluded state. For example, the use of radially expandable stents in endovascular applications is well known, as exemplified by U.S. Pat. Nos. 4,733,665, 4,739,762, 4,776,337, and 4,793,348 relating to balloon expandable endoluminal stents, all issued to Palmaz, et al., U.S. Pat. Nos. 4,580,568, 4,800,882, 4,907,336, 5,035,706, 5,041,126, and 5,282,824 relating to balloon expandable and self-expanding endoluminal stents, all issued to Gianturco, et al., all of which are hereby incorporated by reference for the purpose of exemplifying stent types useful with the longitudinally reinforced grafts of the present invention.

The use of radially expansible stents is not, however, limited to endovascular applications. Rather, various types of endoluminal stents are also employed to maintain other anatomical passageways, such as biliary ducts and ureters in an unoccluded condition. In those uses where it may be desirable to cover the stent with a biocompatible material, particularly one which will promote tissue ingrowth, such as PTFE, the stent is covered with the biocompatible material. In the endovascular interventional medical field, endovascular stents may be covered by co-axially disposing a tubular PTFE vascular graft over an endovascular stent, the stent-graft assembly is introduced endovascularly and delivered to the desired location, whereupon the stent-graft assembly is radially expanded, such as by balloon dilatation to secure the stent-graft assembly against the vessel walls.

Balloon expansion of the stent-graft assembly occurs at pressures sufficient to cause both the stent and the graft to radially expand. As used herein, the terms "axial shrinkage" and "axial foreshortening" are used interchangeably to describe a reduction in the longitudinal length of the graft alone or the graft relative to the longitudinal length of the stent which occurs upon radial expansion of the graft or the graft-stent combination. Axial shrinkage of the graft relative to the associated stent typically results in exposure of the proximal and/or distal end of the stent. Such exposure may, in turn, provide a fluid passageway for body fluids, such as blood, to flow between the abluminal wall of the graft and the luminal wall of the anatomical passageway, e.g., a blood vessel. Such an escaping flow as in, for example, an arteriovenous fistula repair, is undesirable and may be associated with increased mortality and decreased patency of the graft or stent-graft. It is desirable, therefore, to provide a tubular PTFE structure which is resistant to axial shrinkage during radial expansion of the PTFE structure.

BACKGROUND OF THE PRIOR ART

The use of coatings, wraps and impregnated materials in conjunction with PTFE vascular gratis is known. However, in the prior art, such coatings, wraps or impregnated materials are used for example, to i) increase the tear strength of the PTFE (Mano, et al., U.S. Pat. No. 4,306,318); ii) enhance endothelialization of the PTFE; iii) enhance mechanical compliance of the PTFE (Gogolewski, U.S. Pat. No. 4,834,747); iv) seal the microporous network present in expanded PTFE (Fleckenstein, et al., U.S. Pat. No. 4,902,290); v) increase radial and longitudinal elasticity of the PTFE graft (Tu, et al., U.S. Pat. No. 5,061,276); vi) provide a self-sealing component to the PTFE graft to seal suture holes or needle punctures (Mano, U.S. Pat. No. 4,304,010); or vii) provide binding sites for pharmacologically active agents (Greco, et al., U.S. Pat. No. 4,749,585; Mano, U.S. Pat. No. 4,229,838).

To date, however, the prior art is devoid of a tubular PTFE structure having means associated therewith to impart a resistance to longitudinal compression or axial shrinkage upon radial expansion of the tubular PTFE structure. The present invention offers a solution to this deficiency in the prior art.

SUMMARY OF THE INVENTION

It is an object of the present invention to provide a means for structurally reinforcing a tubular PTFE structure to impart resistance to longitudinal compression or axial shrinkage which occurs during radial expansion of the tubular PTFE structure.

It is a further object of the present invention to provide at least one substantially longitudinally non-compressible, longitudinally non-compliant structure extending integrally bound and axially positioned along a longitudinal axis of the tubular structure PTFE.

It is a still further object of the present invention to provide at least one reinforcing structure integrally bound and axially positioned along the longitudinal length of the tubular PTFE structure on at least one of a luminal wall surface, an abluminal wall surface or residing within the wall of the tubular PTFE structure.

It is yet a further object of the present invention to provide at least one reinforcing structure made of a biocompatible melt thermoplastic which is integrally bound to the microporous matrix used to make the vascular graft.

It is a still further object of the present invention to provide at least one reinforcing structure made of a melt thermoplastic having a melt viscosity sufficient to penetrate the microporous matrix of expanded polytetrafluoroethylene.

It is a still further object of the present invention to provide a reinforcing structure made of a solvent borne, thermoplastic or photo-curable plastic capable of integrating into interstices in expanded polytetrafluoroethylene.

It is yet another object of the present invention to provide a reinforcing structure made of plastic materials selected from the group consisting of polyamides, polyimides, polyesters, polypropylenes, polyethylenes, polyfluoroethylenes, polyvinylpyrolidones, fluorinated polyolefins such as fluorinated ethylene/propylene copolymers ("FEP") such as tetrafluoroethylene/ hexafluropropylene copolymer, perfluoroalkoxy fluorocarbons ("PFA") such as tetrafluoro-ethyl/perfluoro propyl vinyl ether copolymer, ethylene/tetrafluoroethylene copolymers ("ETFE"), polyvinylpyrrolidone ("PVP") or similar biocompatible plastics which are capable of being bound to expanded PTFE at temperatures below the sintering temperature of PTFE of at least 327° C., such as by cross-linking in the presence of cross-linking agents or mechanical bonding by application of pressure to cause the thermoplastic to flow into the microporous structure of the expanded PTFE substrate.

It is a still further object of the present invention to provide an aqueous dispersion of a reinforcing material which is coated onto an expanded PTFE tubular structure. After coating and drying the reinforcing material onto the expanded PTFE tubular structure the reinforcing material imparts resistance to longitudinal compression or axial shrinkage upon radial expansion of the tubular PTFE structure.

It is yet a further object of the present invention to provide an aqueous dispersion of polytetrafluoroethylene in surfactant, such as polytetrafluoroethylene octyphenoxypolyethoxyethanol, as a coating medium for coating the dispersion onto an expanded PTFE tubular structure.

It a still further object of the present invention to provide a structural reinforcement member made of a bio-compatible metal or plastic, either co-extruded with or integral with the tubular PTFE structure, to impart resistance to longitudinal compression or axial shrinkage which occurs during radial expansion of the tubular PTFE structure.

Another object of the present invention is to provide an apparatus for manufacturing the longitudinally non-compliant PTFE tubular structure and a method of manufacture thereof, employing a tubular mandrel for carrying the tubular PTFE structure, the mandrel having a plurality of openings passing through the tubular mandrel and communicating between a mandrel lumen and an outer surface of the mandrel, a generally cylindrical mold having a plurality of longitudinal grooves, whereby the expanded PTFE tubular structure is mounted onto the mandrel, the generally cylindrical mold is then concentrically disposed about the tubular PTFE structure and mandrel, there being tight tolerances between the components of the assembly. A melt thermoplastic, such as FEP, is injected into and through the longitudinal grooves in the mold, and a vacuum is applied through the lumen of the mandrel. The vacuum acts on the melt thermoplastic through the openings in the mandrel and the microporous matrix of the expanded PTFE to draw the melt thermoplastic into the microporous matrix of the expanded PTFE. After cooling the assembly, the assembly is disengaged, and the resulting tubular PTFE structure has a plurality of substantially non-compliant longitudinally oriented reinforcing structures made of the melt thermoplastic integrated with the microporous matrix of the PTFE tubular structure.

These and other objects, features and advantages of the present invention will become more apparent to those skilled in the art when taken with reference to the following more detailed description of the preferred embodiments of the invention in conjunction with the accompanying drawings.

BRIEF DESCRIPTION OF THE DRAWINGS

FIG. 1 is a perspective view of a vascular graft having a reinforcing structure to resist axial shrinkage during radial expansion.

FIG. 2 is a cross-sectional view taken along line 2—2 of FIG. 1.

FIG. 3 is a diagrammatic elevational view of a second embodiment of the present invention illustrating application of a solvent-borne reinforcing structure to a vascular graft.

FIG. 4 is a diagrammatic end elevational view of the second embodiment of the present invention illustrating application of a solvent-borne reinforcing structure to a vascular graft.

FIG. 5 is a perspective view of a third embodiment of the present invention illustrating a plurality of reinforcing rib structures associated with a tubular vascular graft.

FIG. 6 is partially exploded diagrammatic view of the present invention illustrating the method for applying an integral reinforcing structure to a tubular vascular graft.

FIG. 7 is a partial cross-sectional view illustrating a mandrel and a mold used to apply an integral reinforcing structure to a tubular graft in accordance with the method of the present invention.

FIG. 8 is a cross-sectional view taken along line 8—8 of FIG. 7, illustrating a mandrel, mold and vascular graft assembly in accordance with the method of the present invention.

FIG. 9 is a cross-sectional end-elevational view illustrating a second embodiment of the mandrel, mold and vascular graft assembly in accordance with the present invention.

DETAILED DESCRIPTION OF THE PREFERRED EMBODIMENTS

Turning now to FIGS. 1–2, there is illustrated a first preferred embodiment of a vascular graft 10 with structural means 16 for imparting the graft 10 with resistance to longitudinal compression or axial shrinkage operably associated with a tubular graft member 12. Tubular graft member 12 has an outer wall surface 13 and a central lumen 14 defining an inner luminal surface 15. Structural means 16 consists generally of a reinforcing member which is co-extruded with, bonded to or integral with either the outer wall surface 13 or the luminal wall surface 15. Where the structural means 16 is bonded to the graft 10, bonding may be accomplished by a variety of bonding methods. For example, a bond may be created by mechanical means, such as applying positive or negative pressure which causes physical interaction between the structural means 16 and the microporous matrix of the graft member 12. Mechanical bonding may be accomplished by use of melt thermoplastics as the structural means 16, caused to flow under the influence of a heat source, such as ultrasound, resistive heating, laser irradiation, etc. Alternatively, the structural means 16 may be chemically bound, such as by cross-linking agents or biocompatible adhesives, to the tubular graft member 12 during manufacture.

The structural means 16 may further consist of a reinforcing region 19 formed within the graft member 12 wall thickness between the luminal surface 15 and the outer wall surface 13 of the tubular graft member 12. The method used to form the reinforcing member 16 or the reinforcing region 19 will be more fully described hereinafter with reference to the best mode presently known to the inventors hereof.

In accordance with the preferred embodiment of the present invention, the tubular graft member 12 is made of microporous expanded polytetrafluoroethylene (e-PTFE). The method of making microporous e-PTFE prostheses by paste extrusion and expansion of the extrudate is well known in the art. Microporous e-PTFE is comprised of characteristic nodes and fibrils interconnecting the nodes. Interstices between the nodes and fibrils form pores which exist throughout the material matrix of the e-PTFE. E-PTFE vascular grafts have met with considerable acceptance due, in large part, to their biocompatibility and susceptibility to tissue ingrowth into the microporous material matrix.

Tubular vascular grafts made of e-PTFE are well suited for endoluminal use. A principal difficult associated with endoluminal grafts lies in the means used to attach or anchor the endoluminal graft to eliminate displacement of the graft due to body movements or fluid flow through the anatomical passageway in which the graft is placed, e.g., a blood vessel. As exemplified by Barone, et al., U.S. Pat. No. 5,360,443, issued Nov. 1, 1994, which is hereby incorporated by reference, endovascular stents have been used as an anchoring mechanism when sutured to a graft, endovascularly delivered and radially expanded to exclude an abdominal aortic aneurysm. In Barone, a stent is provided at proximal and distal ends of a graft and is sutured thereto, such that a longitudinal section of the stent is uncovered to provide direct contact between the stent and the intima. The entire assembly is delivered using a delivery catheter and expandable balloon. Upon positioning of the stent in the desired endovascular position, the expandable balloon is pressure dilatated. The radially expansive force from the expanding balloon impinges upon the endovascular stent and causes the stent to radially expand into contact with a luminal surface of the graft and the intimal surface of the vasculature.

When used as a covering for an endovascular stent, an e-PTFE vascular graft is radially expanded contemporaneously with the expansion of the endovascular stent. One particular difficulty associated with balloon expansion of a stent-graft assembly is that the balloon will typically assume an bulbous configuration at each of its proximal and distal ends. Balloon expansion typically forces the graft or the stent-graft assembly into a torroidal shape with the proximal and distal ends flaring away from the central axis of the stent-graft assembly with a relatively narrow center section intermediate the flared distal and proximal ends. This phenomenon occurs because there is little resistance to inflation at each of the proximal and distal ends of the balloon relative to the balloon area covered by the stent-graft assembly. The expansion balloon thus assumes a "dog-bone" configuration with the proximal and distal ends radially expanding to a greater extent that a central region along the longitudinal axis of the stent-graft or graft. The inflation pressure within the balloon exerts a radially expansive force against the balloon along its entire longitudinal axis. However, because the device to be expanded, i.e., a stent-graft assembly or a graff, restrains against radial expansion, the expansion pressures within the balloon act first on the proximal and distal ends which are un-restrained by the device to be expanded, thereby causing the proximal and distal ends to inflate first, causing the dog-boning effect. The resulting effect is that the graft or the stent-graft assembly is non-uniformly radially expanded along its longitudinal axis.

A principal difficulty with stent-graft assemblies, i.e., those in which an endoluminal stent is covered or lined with a graff, lies in the axial foreshortening of the graft relative to the stent upon radial expansion of the stent-graft assembly. Where either a proximal or distal end of the stent is exposed, there is a great probability that the stent will allow body fluids, such as blood in the vascular system or bile where the stent-graft is employed in a biliary duct, to circumvent the stent-graft assembly causing an undesirable leak. Thus, there is an appreciable danger of increased mortality or morbidity where a graft covering longitudinally foreshortens relative to the stent during radial expansion of the stent-graft assembly.

Axial foreshortening of a radially expanded graft complicates endoluminal graft or stent-graft delivery. As the graft is radially expanded and longitudinally foreshortens, there is a bunching phenomenon which occurs. The bunching phenomenon results in a greater density of graft material per area of surface area of the expansion balloon. The result of graft material bunching is to increase expansion pressures required to radially expand the graft or stent-graft assembly to the same diameter over a non-longitudinally foreshortened graff.

To guard against undesirable axial foreshortening of the graft upon radial expansion, the inventive reinforced graft member 12 has at least one reinforcing structural support means 16 operably associated therewith. The reinforcing structural support means 16 may consist of alternative reinforcing structures bonded to, co-extruded with, or integrally incorporated within the graft member 12. In accordance with alternative preferred embodiments of the present invention, the reinforcing structural support means 16 is either molded onto a tubular graft member 12 or coated onto tubular graft member 12 by application of a dispersion solution, either in aqueous or colloidal form.

Regardless of the manner in which the reinforcing structural support means 16 is produced in association with the tubular graft member 12, the reinforcing structural support means 16 will impart resistance to longitudinal compression and axial foreshortening of the tubular graft member 12. The property of resistance to longitudinal compression and axial foreshortening exists irrespective of the force or impetus which causes the longitudinal compression or shrinkage. Thus, the property of resistance to longitudinal compression and axial foreshortening will restrain the tubular graft member 12 during radial expansion of the tubular graft member 12, during application of an externally compressive force, or will operate against recoil properties of the e-PTFE material.

As illustrated in FIGS. 1 and 2, the reinforcing structural support means 16 is either applied to the outer 13 or inner 11 wall surface of the tubular graft member 12 or incorporated as an integral reinforcing region 19 of the material matrix forming the tubular graft member 12. In accordance with this first preferred embodiment of the reinforced vascular graft 10, the reinforcing structural support means 16 is formed of a biocompatible longitudinally incompressible plastic material, such as a melt thermoplastic selected from the group consisting of polyamides, polyimides, polyesters, polypropylenes, polyethylenes, polyfluoroethylenes, polytetrafluoroethylenes, polyvinylpyrolidones, fluorinated polyolefins such as fluorinated ethylene/propylene copolymers ("FEP") such as tetrafluorethylene/hexafluropropylene copolymer, perfluoroalkoxy fluorocarbons ("PFA") such as tetrafluoroethyl/perfluoro propyl vinyl ether copolymer, ethylene/tetrafluoroethylene copolymers ("ETFE") or similar biocompatible plastics which are capable of being integrally bound to expanded PTFE. Alternatively, the reinforcing structural support means 16 may be formed of a curable plastic material, such as polyvinylpyrrolidone, which is curable upon exposure to thermal energy, such as application of laser irradiation, or upon exposure to light, such as a UV curable material. Alternatively, the reinforcing structural support means 16 may be formed of a biological tissue, such as collagen, which is capable of being cured by cross-linking agents into a substantially monolithic structure bonded or integral with the e-PTFE tubular graft material 12.

The reinforcing structural support means 16 may also consist of a metallic wire co-extruded with the e-PTFE tubular graft material 12 and positioned within the wall thickness of the e-PTFE tubular graft material 12.

Alternatively, the metallic wire structural member is capable of being co-extruded with plastic beading, such as non-expanded PTFE, as is known in the wire-making arts where PTFE is employed as an electrical insulating covering for electrical wires, and the co-extruded metal-PTFE beading is then mechanically or chemically bonded to the outer 13 or inner 11 wall surface of the e-PTFE tubular graft material 12.

Those skilled in the art will appreciate that a myriad of biocompatible materials exist which may be molded with or coated onto an e-PTFE tubular graft member. However, optimum material will have a flow viscosity sufficient to penetrate into a microporous nodefibril matrix of e-PTFE having an average pore size of 5-200 microns at temperatures below the sintering temperature of PTFE. In addition, the optimum material must be substantially incompressible, yet pliable to allow for flexion of the resultant vascular graft.

In accordance with the most preferred embodiment and the best mode contemplated for the invention, the reinforcing structural support means 16 consists of at least one of a plurality of low-profile rib members bonded to the inner 11 or outer wall surface 13 of the tubular graft member. Bonding of the rib member is enhanced by driving the material used to form the low profile rib member into the microporous material matrix of the e-PTFE material forming the tubular graft member 12. Integration of at least a portion of the rib member into the e-PTFE microstructure may be accomplished by application of the material used for the reinforcing structural support means 16 under the influence of positive pressure, while simultaneously creating a negative pressure on an opposing wall surface of the tubular graft member, such as within the lumen 14 of the tubular graft member 12. The applied positive and negative pressures cooperate to drive the material used for the reinforcing structural support means 16 into the material matrix of the tubular graft member 12 and create a reinforcing region 19 within the wall of the tubular graft member 12. The method and apparatus for pressure forming the reinforcing region 19 and the structural support means 16 will be more fully described hereinafter with reference to FIGS. 6-9.

It is important that the reinforcing structural support means 16 or the reinforcing region 19 extend along an entire longitudinal length of the tubular graft member 12. In this manner, at least one longitudinal aspect of the tubular graft member 12 is supported by the reinforcing structural support means 16 against longitudinal compression or axial shrinkage.

EXAMPLE 1

A length of e-PTFE vascular graft was mounted on a cylindrical mandrel. A corresponding length of non-expanded PTFE beading was longitudinally applied to the outer wall of the e-PTFE vascular graft. The beading and graft were tied with wire at each end to maintain the positioning of the beading on the graft. A heat gun mounted with a thermal tip, was applied only to the beading to sinter the beading. After untying the wire restraints, the graft is visually inspected. Upon visual inspection, the beading appeared to adhere to the graft. Upon manual inspection, however, the beading could be peeled from the outer wall surface of the graft.

In the second run of the test, a length of e-PTFE vascular graft was mounted onto a cylindrical mandrel. A corresponding length of non-expanded PTFE beading was longitudinally applied to the outer wall surface of the e-PTFE vascular graft and restrained onto the e-PTFE graft with wire ties at each end. The assembly was loaded into a sintering oven preheated to 375° C. for six minutes, after which the assembly was allowed to cool. Upon visual inspection, the beading appeared to be fully adhered to the graft. The graft was mounted onto an angioplasty balloon and expanded. During radial expansion, the beading dislodged from the graft.

A third run of the test was attempted using FEP tubing having an inner diameter of 0.020 inches (7.9 mm) and an outer diameter of 0.035 inches (13.8 mm). The FEP tubing was longitudinally applied to the outer wall surface of a length of e-PTFE vascular graft mounted onto a cylindrical mandrel. The FEP tubing was restrained by helically winding high temperature PTFE tape about the entire length of the e-PTFE graft and FEP tubing. The wrapped assembly was placed into a sintering oven preheated to 375° C. for six minutes. During heating, the FEP tape unraveled and the FEP melted and beaded on the e-PTFE graft.

A fourth run of the test was conducted, substituting TEFLON thread tape for the high temperature PTFE tape and heating conducted at 265° C., the melt point of FEP, for 5 minutes. The FEP tubing did not melt or stick to the e-PTFE graft.

Successive runs of the test were conducted, each repeating the steps of the fourth test run, but increasing the heating temperature 10° C. with each run. It was not until heating was performed at 295° C. that the FEP melted and adhered to the graft. The FEP-adhered graft from this final test was mounted onto a PALMAZ stent and radially expanded using an angioplasty balloon. Upon radial expansion on the PALMAZ stent, the FEP longitudinal segment maintained adhesion to the graft and did not exhibit any measurable foreshortening from the non-radially expanded condition.

Turning now to FIGS. 3-4, there is described a process for applying a coating of a material used to form the reinforcing structural support means 16. In this second preferred embodiment of the present invention, a tubular graft member 20 is co-axially mounted onto a rotatable mandrel 22. The rotatable mandrel is, in turn, operably coupled to a drive motor 26 which imparts a rotational force to the rotatable mandrel 22. The material used to form the reinforcing structural support means 16 is carried in a dipping tank 24. In this embodiment of the invention, the reinforcing material is formed as one of an aqueous dispersion, a solvent-borne system, or a colloidal suspension of polymerization monomers in the presence of cross-linking agents or photo curing agents. In either case, the reinforcing material is applied in a fluid condition as a coating onto at least one continuous longitudinal section of the outer wall surface 13 of the tubular graft member 20. After coating, the reinforcing material is cured by application of thermal energy or light energy to form a structural coating on the outer wall surface 13 of the tubular graft member 20. Prior to curing, the fluid coating may be driven into the microporous e-PTFE matrix of the tubular graft member 20 by drawing a negative pressure from the central lumen 14 of the tubular graft member 20.

EXAMPLE 2

An e-PTFE vascular graft was made resistant to axial foreshortening by coating the outside surface of the graft with polytetrafluoroethylene octyphenoxy-polyethoxyethanol aqueous dispersion (FLUON AD-1, ICI Advanced Materials). The FLUON AD-1 aqueous dispersion contains negatively charged PTFE particles having a mean size in the range of 0.1-0.3 microns. The aqueous dispersion constitutes about 60% PTFE by weight and is stabilized with non-ionic surfactants.

A 3 mm outer diameter thin-wall IMPRA graft, 25 cm in length was dipped in FLUON AD-1 to wet the outside surface of the graft. The graft was air dried, blow dried and sintered at 375° C. for four minutes.

Longitudinal compression was measured by placing two reference markings one inch apart, manually compressing the uncoated and coated graft on a mandrel to the greatest extent possible and then measuring the distance between the reference markings after compression.

The pre-coating initial length was 1.3 inches and was manually compressible to 0.5 inches. Post-coating, the uncompressed length was 1.35 inches and was manually compressible to 0.98 inches, yielding longitudinally compressibility of 61.5% pre-coating and 27.4% post-coating. Peak radial expansion pressure was 8 Atm and remained unchanged for the coated and the uncoated grafts.

To facilitate loading of the fluid-state reinforcing agent onto the e-PTFE graft, the tubular e-PTFE graft may, alternatively, be a carbon-containing graft. In this embodiment, the component of the carbon-containing graft is used as an adsorbent for the fluid-state reinforcing agent. After adsorption onto the carbon contained within the e-PTFE microporous matrix, the fluid-state reinforcing agent may be processed as described above to form the reinforcing structural support means 16. Carbon-containing PTFE grafts are a variant of vascular grafts in which the e-PTFE microporous matrix has micro particulate carbon, such as activated carbon, dispersed throughout the matrix, or lining the luminal or abluminal walls thereof. A preferred process for producing a carbon-containing graft is more fully described in co-pending U.S. patent application Ser. No. 08/311,497, filed Sep. 23, 1994, filed by McHaney, et al., and co-owned by the assignee hereof, which is hereby expressly incorporated by reference for the purposes of setting forth a process for making a carbon-containing vascular graft and a carbon-containing vascular graft produced by such process.

Turning now to FIGS. 5 and 6, there is disclosed a third embodiment of the invention in which there is a graft member 30 having a central lumen 32 and at least one of a plurality of longitudinally extending rib members 36. The graft member 30 is made in accordance with the extrusion process described in co-pending application Ser. No. 08/134,072, filed Oct. 8, 1993 by R. Kalis, which is commonly assigned to the assignee hereof, and which is incorporated by reference. Under the Kalis co-pending application, a tubular e-PTFE graft is formed with integral rib structures by extrusion of a PTFE billet, expansion and sintering. In accordance with the preferred embodiment of the present invention, the plurality of longitudinally extending rib members 36 are densified by application of thermal energy to only the rib members 36 without exposing the e-PTFE tubular graft wall surface 33 to thermal energy sufficient to densify the wall surface 33. The thermal energy may include selective heating of the rib members 36 or selective cooling of the rib members 36 during longitudinal expansion of the graft to restrain the rib-members from expansion. This third preferred embodiment of the present invention also contemplates that the rib members 36 are selectively integrated with a reinforcing structural support means 16. After curing the reinforcing structural support means 16, each of the plurality of rib members 32 operate as structural support members which resist longitudinal compression or shrinkage of the tubular graft member 30.

EXAMPLE 3

A 4 mm inner diameter single ribbed graft made in accordance with the process described in co-pending Kalis patent application Ser. No. 08/134,072, was obtained and sectioned into ten 3 inch (7.62 cm) sections. Two reference markings were placed in the center of each 3 inch (7.62 cm) section, one inch (2.54 cm) apart, and each sample was loaded onto a 3.56 mm outside diameter mandrel. The samples were longitudinally compressed manually to the greatest extent possible and the distance between the reference markings measured. The samples were then returned to their original 3 inch length. Seven of the samples were again mounted onto a single 3.56 mm OD mandrel, and each sample was secured to the mandrel with wire ties. A Weller Model EC2001 soldering gun was set to 745° F. The tip of the soldering iron was run down the rib of each of the seven samples using slight pressure until the rib began to melt and malform. After cooling, each graft was longitudinally compressed manually on the mandrel and the extent of compression measured by measuring the distance between the two reference markings. Qualitatively, the densified ribs were very stiff and required application of more pressure to compress than the pre-densified ribbed grafts. Table 1, below, summarizes the results of the pre-densification and post-densification longitudinal compression measurements:

TABLE 1

| Sample | Pre-Densification Compression (% Original Length) | Post-Densification Compression (% Original Length) |
| --- | --- | --- |
| A | 61.9 | 58 |
| B | 64.95 | 59 |
| C | 67.30 | 62 |
| D | 64.75 | 65 |
| E | 66.45 | 67 |
| F | 64.35 | NT |
| G | 64.95 | NT |
| H | 66.85 | NT |
| I | 64.25 | NT |
| J | 67.45 | NT |
| AVG | 65.2 STD 1.54 | 62.2 STD 3.43 |

NT = Not Tested
STD = Standard Deviation

We turn now to FIGS. 6–9, which illustrate the preferred method for making the reinforced graft 10 of the present invention. With particular reference to FIGS. 6–8, there is illustrated an vacuum molding assembly 50 for making the inventive reinforced graft 10 of the present invention. Vacuum molding assembly 50 consists generally of a molding mandrel 52 and a vacuum mandrel 62. Vacuum mandrel 62 consists generally of a rigid tubular member having a central vacuum lumen 64 and a plurality of vacuum ports 66 which pass through the rigid tubular member and communicate between the central vacuum lumen 64 and an outer surface of the vacuum mandrel 62. Vacuum mandrel 62 has a vacuum connection, such as a hose barb (not shown), for connecting a vacuum line to the vacuum mandrel 62 such that a negative pressure may be drawn through the plurality of vacuum ports 66 and the central vacuum lumen 64. Vacuum mandrel 62 has an outer diameter having a close fit tolerance with an inner diameter of a tubular graft member 60 such that the tubular graft member 60 may be co-axially engaged thereupon and readily removed therefrom. As an alternative to the plurality of vacuum ports 66, various configurations of opening passing through the vacuum mandrel 62 may be employed. For example, at least one of a plurality of longitudinal slots (not shown) may be formed in the vacuum mandrel 62. So long as at least one entire longitudinal section of the tubular graft member 60 is exposed to a negative pressure from the central vacuum lumen 64, any configuration of suitable vacuum openings may be employed.

The vacuum molding mandrel 52 has at least one of a plurality of injection ports 54 and at least one mold recess 56 in an inner luminal wall surface of the molding mandrel 52. The at least one mold recess 56 extends the entire longitudinal axis of the molding mandrel 52 and is in fluid flow communication with the plurality of injection ports 54.

In operation, a tubular graft member 60 is mounted onto the vacuum mandrel 62, and the graft 60 mounted vacuum mandrel 62, is co-axially disposed within the lumen of the molding mandrel 52. A negative pressure is applied to the vacuum mandrel 62 and a fluid state reinforcing material (not shown) is injected, under positive pressure, through the plurality of injection ports 54. Upon entering the mold recess 56 through the injection ports 54, the reinforcing material flows along the longitudinal axis of the mold recess 56 and is drawn into the microporous e-PTFE matrix of the tubular graft member 60, thereby forming a reinforcing region within the wall thickness of the tubular graft member 60.

An alternative embodiment of the molding assembly 80 is illustrated with reference to FIG. 9. As illustrated in FIG. 9, a mold block member 82 and mold cover member 86 are employed. Mold block member 82 has a mold cavity 84 formed therein, while mold cover member 86 has a molding cover cavity 88 formed therein. The mold cover member 86 has at least one fluid flow opening 90 passing from external the mold cover member 86 to the mold cover cavity 88. Fluid flow opening 90 is used to introduce the reinforcing material, in a fluid state, into the mold cover cavity 88 such that it contacts a tubular graft member 60 resident in the mold cover cavity 88 and the mold cavity 84. As with the abovedescribed embodiment, the tubular graft member 60 is carried co-axially on a vacuum mandrel 92 having a vacuum opening 96 passing through at least a portion of the mandrel wall. Vacuum opening 96 communicates between a central vacuum lumen 98 and an outer surface of the vacuum mandrel 92. Where the vacuum opening 96 is formed of a longitudinal slot in the vacuum mandrel 92, or where the vacuum opening 96 is sufficiently large to cause a large surface area of the tubular graft member 60 into the vacuum opening 96, thereby creating an increased risk of tearing or puncturing the tubular graft member 60, it is desirable to co-axially interdispose a permeable tubular backing member 92 between the tubular graft member 60 and the vacuum mandrel 94. Permeable tubular backing member 92 reinforces the tubular graft member 60 and protects it against tearing or puncturing by impingement upon the edges of the vacuum opening 96, but is sufficiently permeable to permit drawing a negative pressure through it to cause the fluid reinforcing material to penetrate the microporous matrix of the tubular graft member 60.

Those skilled in the art will understand and appreciate that while the present invention has been described with reference to its preferred embodiments, and the best mode known to the inventors for making the preferred embodiments, various substitutions of materials, processing steps and process parameters may be made without departing from the spirit and scope of the invention, which is to be limited only by the appended claims.

What is claimed is:

1. A polytetrafluoroethylene graft, comprising:
a tubular graft member formed of expanded polytetrafluoroethylene having a plurality of nodes and fibrils interconnecting the nodes, and forming a microporous material matrix; and
structural support means for imparting resistance to longitudinal compression or axial shrinkage of the tubular graft member 12. reinforcing the microporous material matrix along a longitudinal axis of the tubular graft member, the structural support means being integrated into at least a portion of the microporous material matrix of the tubular graft member and extending axially along a substantial longitudinal section of the tubular graft member.

2. The graft of claim 1, wherein said structural support means further comprises a rib member bonded to at least one of an outer wall surface and an inner wall surface of the tubular graft member.

3. The graft of claim 2, wherein said rib member further comprises a biocompatible plastic selected from the group consisting of polyamides, polyimides, polyesters, polypropylenes, polyethylenes, polyfluoroethylenes, polyvinylpyrolidones, fluorinated polyolefins, fluorinated ethylene/propylene copolymers, tetrafluorethylene/ hexafluropropylene copolymer, perfluoroalkoxy fluorocarbons, tetrafluoroethyl/perfluoro propyl vinyl ether copolymer, ethylene/tetrafluoroethylene copolymers, and polyvinylpyrrolidone.

4. The graft of claim 1, wherein said structural support means further comprises an aqueous dispersion of a biocompatible polymer in a coating medium, said aqueous dispersion being applied to at least one of an inner wall surface and an outer wall surface of said tubular graft member.

5. The graft of claim 1, wherein said structural support means further comprises a metal member co-extruded with said tubular graft member.

6. The graft of claim 1, wherein said structural support means further comprises a metal member co-extruded with a polytetrafluoroethylene beading member, said polytetrafluoroethylene beading member being sintered onto said tubular graft member.

7. The graft of claim 1, wherein said structural support means provides resistance to at least one of longitudinal compression and axial shrinkage of the tubular graft member, said compression of said graft being less than or equal to about 27 percent of the uncompressed length of said graft.

8. The graft of claim 1, wherein said structural support means further comprises a region integral within the wall thickness of said tubular graft member.

9. An expanded polytetrafluoroethylene endoluminal graft, comprising:
a radially expandable tubular expanded polytetrafluoroethylene graft member characterized by a microporous material microstructure of nodes interconnected by fibrils and having a first unexpanded diameter and a second radially expanded diameter greater than the first unexpanded diameter; and
a structural support member joined to the graft member, oriented substantially parallel to and extending substantially along an entire longitudinal axis of the tubular graft member, thereby providing longitudinal support to the graft member to restrict longitudinal foreshortening of the graft member during radial expansion of the graft member from the first unexpanded diameter to the second radially expanded diameter.

10. The expanded polytetrafluoroethylene endoluminal graft according to claim 9, further comprising a radially expandable stent member joined in intimate contact with the radially expandable tubular expanded polytetrafluoroethylene graft member.

11. The expanded polytetrafluoroethylene endoluminal graft according to claim 10, wherein the radially expandable stent member is joined to a luminal surface of the radially expandable tubular expanded polytetrafluoroethylene graft member.

12. The expanded polytetrafluoroethylene endoluminal graft according to claim 10, wherein the radially expandable stent member is joined to an abluminal surface of the radially expandable tubular expanded polytetrafluoroethylene graft member.

13. The expanded polytetrafluoroethylene endoluminal graft according to claim 9, wherein the structural support member further comprises a rib member bonded to at least one of an outer wall surface and an inner wall surface of the tubular graft member.

14. The expanded polytetrafluoroethylene endoluminal graft according to claim 13, wherein the rib member further comprises a biocompatible plastic selected from the group consisting of polyamides, polyimides, polyesters, polypropylenes, polyethylenes, polyfluoroethylenes, polyvinylpyrolidones, fluorinated polyolefins, fluorinated ethylene/propylene copolymers, tetrafluoroethylene/hexafluoropropylene copolymer, perfluoroalkoxy fluorocarbons, tetrafluoroethyl/perfluoro propyl vinyl ether copolymer, ethylene/tetrafluoroethylene copolymers, and polyvinylpyrrolidone.

15. The expanded polytetrafluoroethylene endoluminal graft according to claim 9, wherein the structural support member further comprises an aqueous dispersion of a biocompatible polymer in a coating medium, said aqueous dispersion being applied to at least one of an inner wall surface and an outer wall surface of said tubular graft member.

16. The expanded polytetrafluoroethylene endoluminal graft according to claim 9, wherein the structural support member further comprises a metal member co-extruded with said tubular graft member.

17. The expanded polytetrafluoroethylene endoluminal graft according to claim 9, wherein the structural support member further comprises a metal member co-extruded with a polytetrafluoroethylene beading member, said polytetrafluoroethylene beading member being sintered onto said tubular graft member.

18. The expanded polytetrafluoroethylene endoluminal graft according to claim 9, wherein the structural support member provides resistance to at least one of longitudinal compression and axial shrinkage of the tubular graft member, said compression of said graft being less than or equal to about 27 percent of the non-compressed length of said graff.

19. The expanded polytetrafluoroethylene endoluminal graft according to claim 9, wherein the structural support member further comprises a region integral within the wall thickness of said tubular graft member.

* * * * *